(12) United States Patent
Giersch

(10) Patent No.: US 6,169,212 B1
(45) Date of Patent: Jan. 2, 2001

(54) BICYCLIC KETONES AND THEIR USE IN THE FIELD OF PERFUMERY

(75) Inventor: Wolfgang Klaus Giersch, Bernex (CH)

(73) Assignee: Firmenich SA, Geneva (CH)

( * ) Notice: Under 35 U.S.C. 154(b), the term of this patent shall be extended for 0 days.

(21) Appl. No.: 09/422,637

(22) Filed: Oct. 22, 1999

(30) Foreign Application Priority Data

Oct. 26, 1998 (CH) .................................................. 2155/98

(51) Int. Cl.[7] .......................... C07C 49/105; C07C 33/02
(52) U.S. Cl. ............................................ 568/374; 568/849
(58) Field of Search ................................... 568/374, 377, 568/849

(56) References Cited

U.S. PATENT DOCUMENTS

| | | | |
|---|---|---|---|
| 3,265,739 | * | 8/1966 | Blumenthal . |
| 3,847,993 | * | 11/1974 | Hall et al. . |
| 3,929,677 | | 12/1975 | Hall et al. ............................ 252/522 |
| 4,181,683 | * | 1/1980 | Tsuji . |
| 5,163,453 | * | 11/1992 | Bachmann et al. . |
| 5,707,961 | | 1/1998 | Bajgrowicz et al. .................. 512/17 |

FOREIGN PATENT DOCUMENTS 0 743 297   11/1996 (EP) .

OTHER PUBLICATIONS

CA:114:121772 abs of EP379981, Aug. 1990.*

* cited by examiner

*Primary Examiner*—Jean F Vollano
(74) *Attorney, Agent, or Firm*—Pennie & Edmonds LLP

(57) ABSTRACT

The compounds of formula (I)

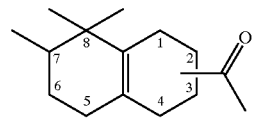

wherein the acetyl substituting group is either in position 2 or in position 3 of the cycle, or any mixture of compounds of formula (I) are novel compounds which can namely confer a natural odor of the leather type to products or compositions to which they are added.

6 Claims, No Drawings

BICYCLIC KETONES AND THEIR USE IN THE FIELD OF PERFUMERY

BRIEF SUMMARY OF THE INVENTION

The present invention relates to novel compounds useful in the field of perfumery. It concerns more particularly the compounds of formula

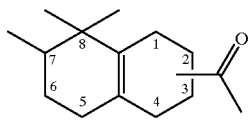

(I)

wherein the acetyl substituting group is either in position 2 or in position 3 of the ring, or any mixture of compounds of formula (I). Any further reference to a compound of formula (I) in the present application will designate either one or the other structural isomer or a mixture of both.

The compounds (I) possess odor properties which are very useful and appreciated. Therefore, they can be used for the preparation of perfumes, perfuming compositions and perfumed articles. These compounds can namely confer odor effects of the natural leather type.

BACKGROUND OF THE INVENTION

The compounds according to the present invention are novel.

The use in the field of perfumery of compounds having a structure close to that of the compounds (I) is known in the prior art. One can cite the patents U.S. Pat. No. 3,929,677 and EP 743 297 which disclose such compounds and discuss their odor properties.

DETAILED DESCRIPTION OF THE INVENTION

Surprisingly, we have now been able to establish that the compounds of formula (I) have a fragrance of a totally original character compared with the odor of known compounds. In fact, the odor of the compounds (I) constitutes an ensemble of woody, powdery-violet, ambergris, slightly marine seaweed type notes, accompanied with a very natural and really unexpected leather type connotation, reminiscent of the odor of fresh Suede leather. This last connotation really distinguishes the compounds of the present invention from the products of similar structure which are described in the prior art, thus conferring to said compounds a great value for their use in perfumery.

The compounds according to the present invention thus make it possible to confer, improve, enhance or modify the odor of consumer products, as well as perfuming bases or concentrates. In other words, they can impart to the latter their characteristic odor, as the case may be modifying and/or improving the original odor properties of the products and compositions in which they are incorporated. These products thus become more appealing to the consumer and have an enhanced odor impact.

The compounds of the invention can be used in fine perfumery, namely in perfumes, colognes, or after-shave lotions, as well as in other current uses in perfumery, namely to perfume soaps, shower or bath gels, hygiene or hair care products such as shampoos and also body or ambient air deodorants and cosmetic preparations.

The compounds (I) can also be used in applications such as liquid or solid detergents for textile treatment, fabric softeners, or yet detergent compositions or cleaning products for dishes or varied surfaces.

In these applications, said compounds (I) can be used alone as well as mixed with other perfuming ingredients, solvents or additives commonly used in perfumery. The nature and variety of these coingredients do not require a more detailed description here, which would not be exhaustive anyway. In fact, a person skilled in the art, having a general knowledge, is able to choose them according to the nature of the product that has to be perfumed and the olfactory effect sought.

These perfuming coingredients belong to varied chemical groups such as alcohols, aldehydes, ketones, esters, ethers, acetates, nitrites, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books.

The proportions in which the compounds according to the invention can be incorporated in the different products mentioned above vary in a broad range of values. These values depend on the nature of the product that has to be perfumed and on the olfactory effect sought, as well as on the nature of the coingredients in a given composition when the compounds of the invention are used in admixture with perfuming coingredients, solvents or additives commonly used in the art.

For instance, concentrations from 5 to 10% by weight, or even 20% by weight, of the compounds of the invention, relative to the weight of the perfuming composition in which they are incorporated, can be used. Much lower concentrations than these can typically be used when these compounds are directly applied for perfuming some of the consumer products mentioned above.

The invention also relates to a process for the preparation of the compounds of formula (I). According to the process of the invention, an alcohol of formula

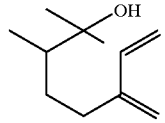

(II)

is subjected to a Diels Alder type reaction in the presence of a methylvinyl ketone, and this reaction is followed by dehydration and cyclisation. These three steps are effected in a one pot "cascade" reaction.

The alcohol of formula (II) is a novel compound and constitutes another object of the present invention. The latter can be obtained by a Grignard type reaction, starting from epoxymyrcene.

The whole synthesis can be described as follows:

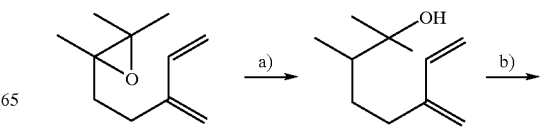

-continued

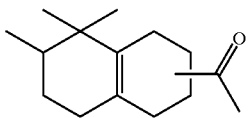

a) CH₃MgCl/tetrahydrofurane, catalyst CuBr, (iso-C₃H₉)₂O
b) But-1-en-3-one, BF₃ ethyl-ether, toluene The reaction conditions are described in more detail in an example presented hereafter.

The invention will now be described in greater detail in the following examples, wherein the temperatures are indicated in degrees centigrade and the abbreviations have the usual meaning in the art.

EXAMPLE 1

Preparation of 1-(1,2,3,4,5,6,7,8-octahydro-7,8,8-trimethyl-2-naphtalenyl)-1-ethanone a) 1230 ml of a solution of CH₃MgCl 3M in tetrahydrofurane (Fluka) was added to 26.5 g of CuBr (Fluka) in 1 l of diisopropylether with stirring at 0° (bath temperature). After one night, the reaction mixture was cooled to −20° and 467 g of epoxymyrcene [2-(3,4-epoxy-4-methylpentyl)-1,3-butadiene] in 4 l of isopropylether were added dropwise. After the addition, the reaction mixture was warmed to room temperature. After 23 h the reaction was completed. After hydrolysis with a 15% NH₄Cl-solution and washing with brine, the product was distilled to obtain 96.6% pure 2,3-dimethyl-6-methylene-7-octen-2-ol with a yield of 453.7 g (88%).

Boiling point: 75°/40 Pa

Spectral data of 2,3-dimethyl-6-methylene-7-octen-2-ol

NMR($^1$H): 0.95(d, J=6,8, 3H); 1.16 and 1.17(2s, 6H); 5.01(s, 2H); 5.06(d, J=11,2, 1H); 5.23(d, J=17,6, 1H); 6.37 (dd, J₁=11,2, J₂=17,6, 1H)

NMR($^{13}$C): 14.5(q); 26.2(q); 27.1(q); 30.1(t); 30.3(t); 44.2(d); 73.4(s); 113.2(t); 115.7(t); 138.9(d); 146.6(s)

MS: 168(M⁺, 0), 153(1), 150(4), 135(9), 107(7), 95(12), 81(21), 68(49), 59(100), 41(37)

b) To a solution of the product obtained under a) (300 g), but-1-en-3-one (147.5 g; Fluka) and toluene (3 l) were added with BF₃.ethylether (30 ml) under stirring. The exothermic reaction increased the temperature of the reaction medium from 23° to 33°. The latter was then heated to 40°. After 22 h, the Diels-Alder type reaction was completed. Again some BF₃.ethylether was added; the reaction mixture became brown, and then dark brown after 45 h. The reaction mixture was washed with a 10% NaOH solution and brine, and then distilled to provide the desired product in the form of a mixture of compounds comprising 1-(1,2,3,4,5,6,7,8-octahydro-7,8,8-trimethyl-2-naphtalenyl)-1-ethanone (2 diastereomers) and 1-(1,2, 3,4,5,6,7,8-octahydro-5,5,6-trimethyl-2-naphtalenyl)-1-ethanone. The yield was 258.2 g (65%).

Spectral data of the products which have been elucidated after separating the mixture via gas chromatography:

Cis-1-(1,2,3,4,5,6,7,8-octahydro-7,8,8-trimethyl-2-naphtalenyl)-1-ethanone

NMR($^1$H): 0.88(d, J=6, 3H); 0.89(s); 1.02(s); 2.17(s)

NMR($^{13}$C): 16.4(q); 22.7(q); 25.2(t); 26.6(t); 26.9(t); 27.8 (q); 28.4(q); 29.2(t);30.5(t); 37.2(s); 39.3(d); 48.8(d); 126.8 (s); 132.8(s); 212.6(s)

MS: 220(M⁺, 35), 205(40), 177(57), 161(14), 135(20), 119(23), 107(38), 91(69), 43(100)

Trans-1-(1,2,3,4,5,6,7,8-octahydro-7,8,8-trimethyl-2-naphtalenyl)-1-ethanone

NMR($^1$H): 0.89(d, J=6, 3H); 0.82 et 0.97(2s, 6H); 2.19(s, 3H)

NMR($^{13}$C): 17.0(q); 20.5(q); 25.5(t); 25.7(q); 27.2(t); 27.6(t); 28.5(q); 31.1(2t); 39.7(d); 49.2(d); 127.2(s); 134.2 (s); 213.0(s)

MS: 220(M⁺, 38), 205(42), 177(57), 161(14), 135(22), 119(24), 107(41), 91(67), 43(100)

Cis-1-(2-isopropyl-2-methyl-1-oxaspiro[4.5]dec-8-yl)-1-ethanone

NMR($^1$H): 0.84 and 0.92(2d, J=6,8, 6H); 1.06(s, 3H); 2.13(s, 3H)

NMR($^{13}$C): 17.9(q); 18.4(q); 23.3(q); 24.6(t); 25.0(t); 27.6(q); 34.4(t); 37.2(t); 37.9(t); 38.2(t); 38.4(d); 51.1(d); 80.2(s); 85.9(s); 212.2(s)

MS: 238(M⁺, 1), 223(3), 195(100), 177(41), 153(30), 135(30), 119(17), 93(12), 83(12), 43(23)

Trans-1-(2-isopropyl-2-methyl-1-oxaspiro[4.5]dec-8-yl)-1-ethanone

NMR($^1$H) 0.86 and 0.92(2d, J=6,8, 6H); 1.11 (s, 3H); 2.14(s, 3H)

NMR($^{13}$C) 17.9(q); 18.4(q); 23.8(q); 26.5(2t); 28.3(q); 34.19(t); 34.31(t); 37.2(t); 37.9(t); 38.6(t); 50.2(d); 82.5(s); 85.4(s); 211.9(s)

MS: 238(M⁺, 0,5), 223(1), 195(60), 177(23), 153(21), 135(22), 119(14), 93(13), 83(16), 71(17), 43(100)

EXAMPLE 2

Perfuming composition

A base perfuming composition was prepared for a feminine cologne having a flowery-herbaceous character by admixing the following ingredients:

| Ingredients | Parts by weight |
|---|---|
| Hexyl acetate | 20 |
| Benzyl acetate | 150 |
| Carbinol acetate | 20 |
| Citronellyl acetate | 80 |
| Geranyl acetate | 180 |
| Linalyl acetate | 25 |
| Phenylethyl acetate | 50 |
| 1%* cis-3-Hexenol acetate | 40 |
| 10%* Anisic aldehyde | 130 |
| 10%* Allyl amyl glycolate | 20 |
| 10%* Ambrettolide ®[1)] | 80 |
| Methyl anthranilate | 10 |
| 10%* Cetalox ®[2)] | 25 |
| 1%* cis-3-Hexenol | 40 |
| Citronellol | 80 |
| Dihydromyrcenol | 75 |
| 10%* β-Dorinone ®[3)] | 25 |
| 10%* Ethylvanilline | 40 |
| Eugenol | 20 |
| Exaltolide ®[4)] | 170 |
| Firsantol ®[5)] | 10 |
| 10%* Floralozone ®[6)] | 20 |
| Galaxolide ®[7)]50 | 730 |
| Geraniol | 10 |
| Hedione ®[8)] | 600 |
| Helional ®[9)] | 10 |
| 10% Indol* | 10 |
| Iralia ® total[10)] | 10 |
| 10%* Liffarome ®[11)] | 10 |
| Lilial ®[12)] | 260 |
| Lyral ®[13)] | 30 |
| 1%* Rose oxide | 50 |
| 1%* p-Cresol | 30 |
| Phenethylol | 130 |
| Polysantol ®[14)] | 50 |

-continued

| Ingredients | Parts by weight |
|---|---|
| Portugal Brazil orange essential oil | 20 |
| Benzyl salicylate | 100 |
| Cis-3-Hexenol salicylate | 150 |
| Tonalide ®[15] | 60 |
| 10%* Undecalactone gamma | 40 |
| Vanilline | 50 |
| 10%* Ylang extra essential oil | 50 |
| Total | 3700 |

*in dipropylene glycol (DIPG)
[1] 9-hexadecen-16-olide; origin:Givaudan-Roure SA, Vernier, Switzerland
[2] 8,12-epoxy-13,14,15,16-tetranorlabdane; origin:Firmenich SA, Geneva, Switzerland
[3] β-damascone; origin:Firmenich SA, Geneva, Switzerland
[4] pentadecanolide; origin:Firmenich SA, Geneva, Switzerland
[5] 2-methyl-4-(2,2,3-trimethyl-3'-cyclopenten-1-yl)-4-penten-1-ol; origin:Firmenich SA, Geneva, Switzerland
[6] 3-(4-ethyl-1-phenyl)-2,2-dimethylpropanal; origin:International Flavors and Fragrances, USA
[7] origin:International Flavors and Fragrances, USA
[8] methyl dihydrojasmonate; origin:Firmenich SA, Geneva, Switzerland
[9] 1-(4-methoxyphenyl)-1-ethanone; origin:Givaudan-Roure SA, Vernier, Switzerland
[10] methylionone; origin:Firmenich SA, Geneva, Switzerland
[11] cis-3-hexenyl methyl carbonate; origin:International Flavors and Fragrances, USA
[12] 3-(4-ter-buthylphenyl)-2-methylpropanal; origin:Givaudan-Roure SA, Vernier, Switzerland
[13] 4-(4-hydroxy-4-methylpentyl)-3-cyclohexene carboxaldehyde; origin:International Flavors and Fragrances, USA
[14] 3,3-dimethyl-5-(2,2,3-trimethyl-3-cyclopenten-1-yl)-4-penten-2-ol; origin:Firmenich SA, Geneva, Switzerland
[15] 6-acetyl-1,1,3,4,4,6-hexamethyl-tetrahydronaphtalene; origin:Polak's Frutal Works The addition of 300 parts by weight of the compounds of formula (I) according to the invention gives to this flowery-herbaceous base accord a lovely woody-leather connotation which is totally original, and which cannot be achieved by any combination of woody and leathery products known from the prior art.

EXAMPLE 3

Perfuming composition

A base perfuming composition for a masculine cologne of the chypre-leather type was prepared by admixing the following ingredients:

| Ingredients | Parts by weight |
|---|---|
| Geranyl acetate | 5 |
| Linalyl acetate | 70 |
| Bergamot essential oil | 560 |
| Sfuma lemon essential oil | 60 |
| Coumarin | 50 |
| Dihydromyrcenol | 80 |
| Eugenol | 5 |
| Habanolide ®[1] | 480 |
| Hedione ® HC[2] | 100 |
| 10%* Indol | 25 |
| β-Ionone | 5 |
| 10%* Isobutylquinoleine ®[3] | 10 |
| Lyral ®[4] | 250 |
| Sfuma mandarine essential oil | 290 |
| 10%* Mousse cristal | 140 |
| Nutmeg Oil | 30 |
| 10%* trans-1-(2,2,6-Trimethyl-1-cyclohexyl)-3-hexanol[5] | 55 |
| Patchouli oil | 70 |
| Amyl salicylate | 80 |
| Tonalide ®[6] | 400 |
| 10%* Triplal ®[7] | 30 |

-continued

| Ingredients | Parts by weight |
|---|---|
| 10%* Undecalactone gamma | 5 |
| Vertofix Coeur[8] | 400 |
| Total | 3200 |

*in dipropylene glycol (DIPG)
[1] pentadecenolide; origin:Firmenich SA, Geneva, Switzerland
[2] methyl cis-dihydrojasmonate; origin:Firmenich SA, Geneva, Switzerland
[3] origin:International Flavors and Fragrances, USA
[4] 4-(4-hydroxy-4-methylpentyl)-3-cyclohexen-1-carboxaldehyde; origin:International Flavors and Fragrances, USA
[5] origin:Firmenich SA, Geneva, Switzerland
[6] 6-acetyl-1,1,3,4,4,6-hexamethyl-tetrahydronaphtalene; origin:Polak's Frutal Works
[7] 2,4-dimethyl-3-cyclohexen-1-carboxaldehyde; origin:International Flavors and Fragrances, USA
[8] origin:International Flavors and Fragrances, USA The addition of 1000 parts by weight of the compound of formula (I) brings to this masculine chypre-leather composition a pleasant connotation which is very natural and reinforces the woody note conferred by the Vertofix Coeur. On the other hand, the fragrance becomes more masculine.

EXAMPLE 4

Perfuming composition

A base perfuming composition of the spicy-ylang type for a powder detergent was prepared by admixing the following ingredients:

| Ingredients | Parts by weight |
|---|---|
| Verdyl acetate | 40 |
| 50%* Cinnamic alcohol | 70 |
| Anisic aldehyde | 10 |
| 10%* C11 Undecyclic aldehyde | 20 |
| 50%* C12 Aldehyde | 40 |
| 50%* Cinnamic aldehyde | 10 |
| 1%* Phenylacetic aldehyde | 50 |
| 10%* Methyl benzoate | 35 |
| Benzophenone | 100 |
| 4-Cyclohexyl-2-methyl-2-butanol[1] | 120 |
| Dihydromyrcenol | 135 |
| 50%* Habanolide ®[2] | 300 |
| Hedione ®[3] | 70 |
| Heliotropine | 20 |
| 10%* Indolarome ®[4] | 50 |
| Iralia ® total[5] | 250 |
| Lavandin Grosso essential oil | 50 |
| Methylisoeugenol | 20 |
| Methyl-para-cresol | 5 |
| 10%* Methyl octin carbonate | 15 |
| Rose oxide | 15 |
| Phenethylol | 200 |
| Phenylhexanol | 100 |
| Polysantol ®[6] | 100 |
| 9-Decen-1-ol | 25 |
| Terpineol | 70 |
| Vert de Lilas | 5 |
| Ionone alpha | 55 |
| Wardia ®[7] | 20 |
| Total | 2000 |

*in dipropylene glycol
[1] origin:Firmenich SA, Geneva, Switzerland
[2] pentadecenolide; origin:Firmenich SA, Geneva, Switzerland
[3] methyl dihydrojasmonate; origin:Firmenich SA, Geneva, Switzerland
[4] 4,4A,5,9B-tetrahydro-indeno[1,2-D]-1,3-dioxine; origin:International Flavors & Fragrances, USA
[5] methylionone; origin:Firmenich SA, Geneva, Switzerland
[6] 3,3-dimethyl-5-(2,2,3-trimethyl-3-cyclopenten-1-yl)-4-penten-2-ol; origin: Firmenich SA, Geneva, Switzerland
[7] floral composition; origin:Firmenich SA, Geneva, Switzerland The addition of 400 parts by weight of the compound of formula (I) imparted to this composition the woody character that was lacking and distinctly enhanced its impact on dry linen. The natural leather type connotation of the compound of the invention fits particularly well with the spicy-ylang notes of this base fragrance.

What is claimed is:

1. A compound of formula

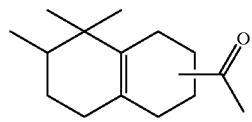

(I)

wherein the acetyl substituting group is either in position 2 or in position 3 of the ring, or any mixture of compounds of formula (I).

2. A method to confer, improve, enhance or modify the odor properties of a perfuming composition or a perfumed product, which method comprises adding as a perfuming ingredient to said composition or product, a compound according to claim 1.

3. A perfuming composition or a perfumed product containing as an active ingredient a compound according to claim 1.

4. A perfumed product according to claim 3, in the form of a perfume or a cologne, an after-shave lotion, a cosmetic preparation, a soap, a shampoo or hair-conditioner or another hair-care product, a bath or shower gel, a body or air deodorant, a detergent or a fabric softener, or a household product.

5. Process for the preparation of a compound according to claim 1, characterized in that a compound of formula

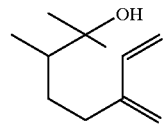

(II)

is subjected to a Diels-Alder type reaction in the presence of a methyl vinyl ketone, followed by dehydration and cyclisation reactions.

6. A compound of formula

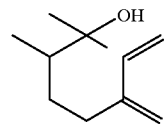

(II)

* * * * *